United States Patent
Krakau et al.

[11] 3,936,162
[45] Feb. 3, 1976

[54] NIGHT VISION TESTING METHOD AND APPARATUS

[76] Inventors: Carl Erik Torsten Krakau, Bengt Lidforss v.1, Lund, Sweden, S-22365; Rolf Gunnar Ohman, Odarslov 88, Lund, Sweden, S-22590

[22] Filed: May 20, 1974

[21] Appl. No.: 471,669

[30] Foreign Application Priority Data
May 23, 1973 Sweden............................. 7307223

[52] U.S. Cl. ...................... 351/17; 351/36; 351/39
[51] Int. Cl.² ............................................ A61B 3/06
[58] Field of Search ..................... 351/1, 17, 36, 39

[56] References Cited
UNITED STATES PATENTS
| | | | |
|---|---|---|---|
| 2,239,164 | 4/1941 | Wigelsworth | 351/17 |
| 2,283,769 | 5/1942 | Schwanzel | 351/17 |

FOREIGN PATENTS OR APPLICATIONS
| | | | |
|---|---|---|---|
| 194,360 | 9/1967 | U.S.S.R. | 351/1 |

Primary Examiner—Paul A. Sacher
Attorney, Agent, or Firm—Limbach, Limbach & Sutton

[57] ABSTRACT

A subject whose vision is to be tested wears a face mask having an eyepiece in which is mounted a light-emitting diode connected to means for varying the light intensity of the diode in a time ordered sequence. The level of light intensity is also numerically displayed to the operator of the device. The test subject is provided with means for selectively stopping and resetting the sequence of varying light intensities to an initial intensity and automatically repeating the cycle.

10 Claims, 3 Drawing Figures

NIGHT VISION TESTING METHOD AND APPARATUS

BACKGROUND OF THE INVENTION

This invention relates to a device and method for testing the mesopic visual acuity of a subject and more particularly to an automated device for giving the dark adaptation vision characteristics of a subject with respect to time.

It is well known that in the nearly complete absence of light, a person's vision is "scotopic," that is, light is perceived primarily by the rods in the eye. In normal daylight vision a person's vision is primarily "phototopic;" the cone vision controls. Intermediate between scotopic and phototopic vision is the range of mesopic vision. If the illumination is suddenly decreased from phototopic levels to mesopic levels, the visual acuity of human beings falls regularly and predictably and then increases with respect to time for a given person, as his eyes adapt to the lower level of illumination. This acuity characteristic is different for each person and can deteriorate with age or illness.

In some prior art visual acuity devices, a person's visual acuity at only a single light level is determined. In still another device, the time required for the subject's vision to adapt to two predetermined light intensities is measured. The problem with these types of devices is that they either only measure a threshold light perception level at some fixed point in time or they measure the time required for the person's eye to adapt to one or more predetermined light intensities. They do not, however, give a complete time based characteristic of the light intensity levels which may be perceived by the subject during a single course of dark adaptation.

Still another problem with many such prior art devices is that they either must be conducted in a darkened room or they require elaborate light excluding shields which are attached to the optical measuring device, thereby making it either uncomfortable for the subject and the observer to use and/or bulky. Since it is sometimes necessary for the subject to look into the testing device for periods of time ranging as long as 15 minutes to half an hour, it is desirable that such devices be comfortable for the subject.

SUMMARY OF THE INVENTION

The above and other disadvantages of such prior art devices are overcome by the present invention of a method and apparatus for night vision testing comprising means for presenting a light display at variable intensities, means for incrementally varying the intensity of the light display in a time ordered sequence, means for displaying a numerical quantification of the intensity of the light display, and means for selectively stopping and resetting the sequence of varying light intensities to an initial light intensity, and automatically repeating the cycle. In one preferred embodiment of the apparatus, the variation in light intensity is a time ordered stepwise increase in the light intensity up to a predetermined level. The light display is provided by means of a light emitting diode fitted into the face plate of an extraneous light excluding face mask which is worn by the subject.

When the apparatus is initially activated, a counter is started and a current of relatively low, predetermined magnitude is delivered to the light emitting diode. In time ordered, stepwise fashion this current magnitude is increased under the control of the counter. The current magnitude is also displayed numerically. The current magnitude is maintained at each step for a period of approximately 1.5 seconds and then the current is increased. In one preferred embodiment, for example, the current magnitude is increased sufficiently between each step to double the light intensity. When the highest level is reached, a pause is made for approximately 6 seconds and the counter is automatically reset to the initial point and the current is reduced again to the lowest level. The counting cycle is thereafter automatically repeated until the subject first perceives the light. The subject is instructed that when he first perceives the light from the diode, he is to press a button switch which halts the counter and presents the current magnitude and hence the light intensity level on the numerical display for approximately 6 seconds. The apparatus thereafter automatically resets and recycles the counter.

Since the counter recycles each time the button is pressed or after it has reached its highest level, the test is repeated numerous times. By stepping the illumination through a large range in a time that is short relative to the dark adaptation process, the apparatus of the invention allows several measurements of sensitivity while the sensitivity of the subject changes only slightly. Such multiple independent measurements provide a better estimate of the subject's true sensitivity than prior art methods and devices which obtain only one or two independent measurements. Thus, the subject's visual acuity with respect to time is numerically determined by the present invention and may be plotted to give a time based characteristic of the subject's dark adaptation and the time required for the subject's visual acuity to reach the mesopic range.

It is, therefore, an object of the present invention to provide an automatic, night vision testing apparatus for determining the dark adaptation characteristic of a subject;

it is another object of the invention to provide a night vision testing apparatus which may be easily and conveniently worn by the subject;

it is still another object of the invention to provide a night vision testing apparatus which gives a numerical display of the light perception of a subject; and it is a still further object of the invention to provide a method for testing the variation in the night vision characteristics of a subject over a predetermined period of time.

The foregoing and other objectives, features and advantages of the invention will be more readily understood upon consideration of the following detailed description of certain preferred embodiments of the invention, taken in conjunction with the accompanying drawings.

DETAILED DESCRIPTION OF THE PREFERRED EMBODIMENT

Figure 1:
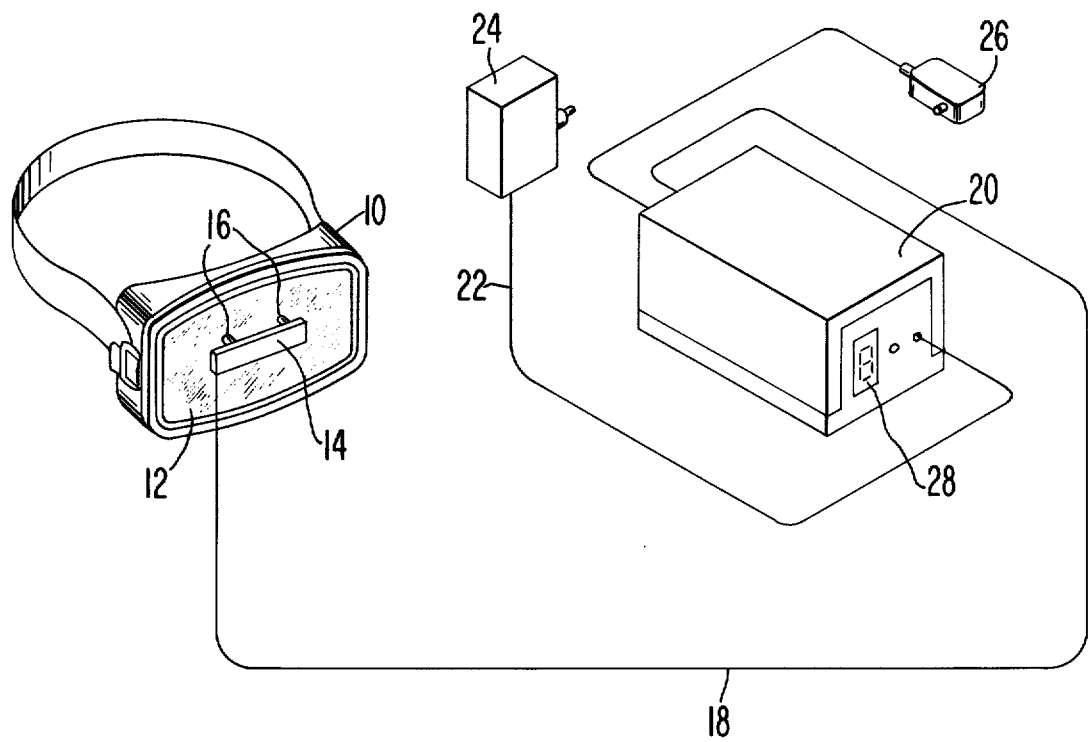
FIG. 1 is a diagrammatic view of the invention.

Referring now more particularly to FIG. 1, the subject whose vision is to be tested is instructed to wear a face mask 10 having a construction which is similar to a diving mask. The mask 10 has a face plate 12 constructed of opaque glass, plastic or the like. The face plate 12 may also be constructed of a material which is transparent in a spectral range which does not affect the subject's light adaptation characteristics, such as a spectral range of red. Attached to the face plate 12 is a frame 14 which supports one or more light emitting devices 16 such as light emitting diodes. Each light emitting diode is aligned with one of the eyes of the test subject. In other embodiments the light emitting diode or other light emitting device is not attached directly to the face mask but instead is connected to it through a fiber optical assembly.

The face mask 10 is designed to be snug fitting to the subject's face in order to exclude extraneous light. This feature allows the test to be taken in a room having ordinary light, although it is preferably not done in strong sunlight. Also a strong light behind the subject should be avoided. Although in the embodiment depicted in FIG. 1 only a single diode may be supplied, the frame 14 is detachable from the face plate 12 so that the orientation of the light emitting diode 16 may be altered from one eye to the other.

In the preferred embodiment, the light emitting diode 16 is connected by means of a pair of wires 18 to the control assembly 20. The control assembly 20 is powered through a wire 22 connected to a plug-in type, rectified power supply 24. A push-button control switch 26 is connected to the control box 20 and is held by the subject whose vision is being tested.

In operation, after the rectifier unit 24 is plugged into a standard power supply and is switched on, a counter within the control box 20 is started and a current, whose magnitude increases in stepwise fashion, is delivered through the wires 18 to the light emitting diodes 16. Each level of current magnitude is represented by a numerical figure display 28 in the control box 20. The current level at each step is maintained for approximately 1.5 seconds then the current is increased by an amount sufficient to double the light intensity. When the highest level is reached, as indicated by the numeral nine in the display 28, a pause is made for approximately 6 seconds before the counter within the control box 20 is automatically reset to zero to begin another cycle of counting.

When the subject first perceives the light emitted by the diode 16 he is instructed to press the button switch 26 which stops the counter within the control box 20. The numerical figure display 28 thus indicates the level of light intensity which is first perceived by the subject and this figure is displayed for approximately 6 seconds before the counter is automatically reset to begin the cycle again.

The testing procedure begins by asking the subject to don the face mask 10. The test is then begun and proceeds through a number of cycles. After about 5 minutes the cycle has been repeated several times. If the same figure repeatedly appears in the display 28 or if the level perceived is improved one or two steps, the threshold value of light perception can thus be determined with sufficient certainty. Alternatively the subject can be instructed to don the face mask and wait 5 minutes before beginning the test.

For a determination of a complete dark adaptation curve of a given subject, it is required that the subject be pre-adapted to a fixed level of illumination in a standardized way. For a simple test, however, the present device may be used to make certain that the subject can perceive light at and under the mesopic level needed for such activities as night driving. For such tests, the pre-adaptation procedure can be omitted provided the subject has stayed for some period of time in a room having ordinary conditions of illumination. In such case, one can assume that the level corresponding to the mesopic region will be reached within approximately 5 minutes for an average subject.

Figure 2:
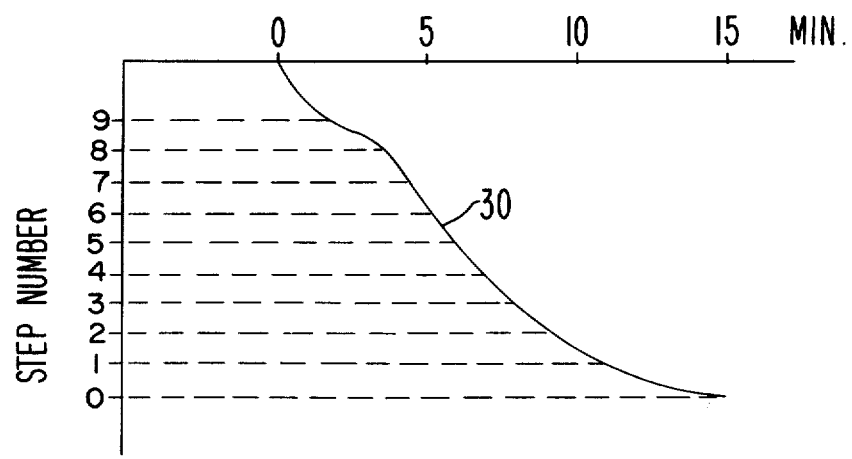
FIG. 2 is an illustrative dark adaptation curve of a hypothetical subject taken with the device of the invention.

Referring now more particularly to FIG. 2, a hypothetical subject's time based perception of 10 illumination levels has been plotted. Level 0 is the least amount of illumination possible and level 9 is the highest level of illumination possible with the device. By repeatedly testing the subject during the dark adaptation process, a curve 30 may be obtained which indicates the level of light intensity perceived at any given period of time from an initial point in time designated "0" in the figure. Thus, approximately 5 minutes after the test has begun, the curve 30 shows that the subject is able to perceive light levels as low as level 4 which, for the purposes of this description, may be designated as the mesopic range, e.g., the range to which one is adapted during driving at night with the vehicle headlights on. As the adaptation testing period is extended to as long as 10 to 115 minutes, the lowest step (0) should be reached if the subject has normal night vision.

One advantage of the present device is that by using a light excluding face mask 10, no darkroom is required. The testing operator can use the period of adaptation for other tasks, such as completing a questionnaire with respect to the subject. Some prior art devices required that a darkened room be used and this presented difficulties for the test operator because he was required to observe and record test results in the dark.

Figure 3:
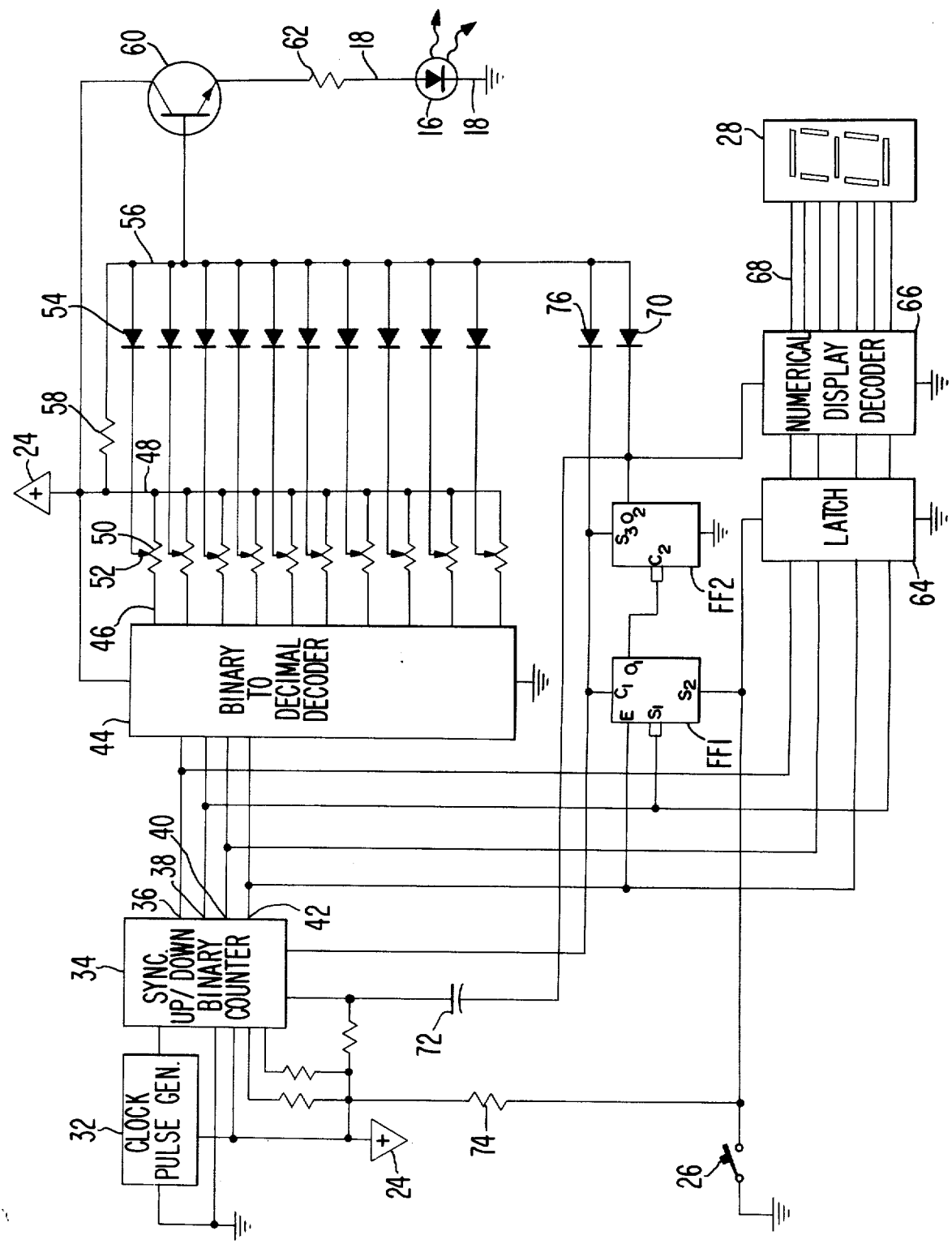
FIG. 3 is a schematic diagram of the embodiment of FIG. 1.

Referring now more particularly to FIG. 3, the contents of the control box 20 are illustrated in greater detail. A clock pulse generator 32 provides an output pulse at a rate of approximately one pulse per second to the input of a synchronous, up/down binary counter 34. The binary coded output from the counter 34 appears at leads 36, 38, 40 and 42 corresponding to the zeroth, first, second and third powers of two, respectively. These output signals from the binary counter 24 on leads 36–42 are fed into the input of a binary-to-decimal decoder 44 which converts the binary outputs into a decimal output which appears on one of ten leads collectively numbered with reference numeral 46. Each one of the 10 output leads 46 corresponds to a particular given number, such as 0, 1, etc., with the last lead corresponding to the number 9.

Each of the leads 46 is connected to a bus 48 through separate potentiometers referred to collectively by the reference numeral 50. The bus 48 is connected directly to the positive (+) terminal of the grounded power supply 24. The sliding contact arm 52 of each potentiometer 50 is connected to the cathode of a separate diode 54 whose anode is connected to a second bus 56. Each potentiometer 50 and sliding contact arm 52 constitutes a voltage dividing network and the contact arms 52 on the potentiometers 50 are set at different positions to provide different voltage levels. The second bus 56 is connected through a resistor 58 to the positive terminal of the power supply 24. The bus 56 is also connected to the base electrode of an NPN transistor 60. The collector electrode of the transistor 60 is connected directly to the positive terminal of the power supply 24 and the emitter electrode is connected in series with a load resistor 62, the light emitting diode 16, and the leads 18 to the circuit ground.

In normal operation, each of the output leads 46, with the exception of one, is "high," meaning that each of the output leads 46 with the exception of one has a voltage level sufficient to reverse bias the particular diode 54 to which it is connected. One of the leads 46 is "low," meaning that it has a voltage level sufficiently below the voltage level supplied to the diode 54 to which it is connected so as to forward bias that particular diode. The forwardly biased diode 54 thus allows the resistor 58 and the particular potentiometer 50 to which it is connected to act as a voltage divider-biasing network to the base electrode of the transistor 60. The particular bias voltage thus supplied to the base electrode of the transistor 60 controls the current flowing between the collector and emitter electrodes of the transistor 60 and thus the current supply to the light emitting diode 16.

Since the intensity of the light emitted from the diode 16 is proportional to the current flowing through it, the control of the base bias on the transistor 60 controls the light intensity level of the light emitting diode 16. As the counter 34 is supplied with pulses from the clock pulse generator 32, it causes the decoder 44 to sequentially de-energize the output leads 46 and thus supply a time ordered sequence of different bias voltages to the base electrode of the transistor 60 in stepwise fashion.

Each of the leads 36, 38, 40 and 42 are connected through a latching unit 64 to separate inputs of a numerical display decoder 66. The decoder 66 converts the binary coded output signals from the counter 34 into appropriately coded signals to operate a seven-segment display 28 and give a decimal, numerical indication of the level of light intensity to be emitted by the diode 16. The signals from the decoder 66 are connected via seven separate leads 68 to the numerical display 28.

A pair of flip-flops FF1 and FF2 are provided in order to control the operation of the device when the end of a count is reached in the counter 34 or when the subject being tested depresses the push-button switch 26. During normal counting, the flip-flop FF1 is "cleared," meaning its output at a lead $0_1$ is at a reduced voltage level while the flip-flop FF2 is "set," meaning that the output appearing at its terminal $0_2$ is at a relatively high voltage level. The output $0_2$ of FF2 is connected to the cathode of a diode 70 whose anode is connected to the second bus 56. The voltage level appearing at the FF2 output $0_2$ when FF2 is set is sufficient to reverse bias the diode 70.

When the binary counter 34 has counted to a level corresponding to the decimal number 10, the lead 42 and the lead 38, corresponding to $2_3$ and $2^1$, will be high, meaning that they carry a relatively high voltage level. The lead 42 is connected to the enabling input E of FF1 and the lead 38 is connected to the set terminal $S_1$ of FF1. When pulses simultaneously appear at the terminals $S_1$ and E of FF1, it is set, producing a voltage output at its terminal $0_1$. The terminal $0_1$ is connected to a terminal $C_2$ of FF2. When the set voltage output first appears at the terminal $0_1$ FF2 is caused to clear, thereby reducing the voltage output at the terminal $0_2$ to a relatively low level which forward biases the diode 70.

When the diode 70 becomes forwardly biased, the potential on the bus 56 is reduced to a level sufficient to cause the transistor 60 to become substantially non-conductive and the light emitting diode 16 is reduced to its lowest level of light intensity. The terminal $0_2$ is also connected to the numerical display decoder 66 and when FF2 clears, it causes the numerical display decoder 66 to freeze and hold its numerical presentation on the display 28.

The transient pulse appearing at the output $0_2$ when FF2 clears is also supplied through a capacitor 72 to a load input L of the counter 34. The result of supplying this pulse to the load input L is to wipe out the existing count and load a predetermined number, such as the number 10, into the counter 34. Since the counter 34 has a capacity to count to 16, it will thereafter continue to count from the loaded number, such as the number 10, to the limit of its capacity, i.e., the number 16. This, in effect, provides a time delay during which time the number on the display 28 is held. Since the clock pulse generator 32 supplies pulses at a rate of approximately one per second, this time delay will amount to approximately 6 seconds during which time the operator of the device may take note of the number in the display 28.

When the counter 34 has reached the end of its capacity, a pulse is generated at its output terminal CL (carry line) which is connected to the terminals $C_1$ and $S_3$ of the flip-flops FF1 and FF2, respectively. The carry line signal supplied to these two input terminals causes FF1 to become clear and FF2 to become set, thereby restoring the flip-flops to their initial states. Likewise, the counter 34 has returned to its initial state and the numerical display decoder 66 will cause the display 28 to indicate the numeral 0. The terminal $S_3$ of FF2 is also connected to the cathode of a diode 76 whose anode is connected to the bus 56. The purpose of this connection is to dim the light emitting diode 16 when the carry line signal is generated during the recycling process.

A set terminal $S_2$ of the flip-flop FF1 is connected through the normally open pushbutton switch 26 to the circuit ground and through a load resistor 74 to the positive terminal of the power supply 24. The terminal $S_2$ is also connected to the latch unit 64. When the switch 26 is depressed and closed by the test subject, the negative going pulse thereby generated at terminal $S_2$ causes FF1 to become set which, in turn, causes FF2 to be cleared. This repeats the sequence of operations described above to hold the numeral in the display 28, to cause the binary counter to be loaded with a number, such as the number 10 and to thereafter count out the remainder of its capacity to provide an approximately 6 second time delay after which the entire system is reset to its initial condition. The purpose of the latch unit 64 is to hold the input to the numerical display decoder 66 constant during the 6 second time delay. In other embodiments, the latch unit may be omitted depending upon the characteristics of the decoder 66.

Although the details of the units 32, 34, 44, 64, 66, FF1 and FF2 are not described in detail, their construction is well known to those skilled in the art. It will also be understood that the particular connections between these units and the power supply 24 are not described in detail other than to say that they are individually connected between the positive terminal of the grounded power supply 24 and the circuit ground.

While certain details of the control unit 20 have been described with reference to FIG. 3, it will be apparent that in other embodiments suitable modifications may be made to carry out the method of the invention described above with reference to FIGS. 1 and 2, namely, testing the night vision of a subject by presenting a light display to him of variable intensities, incrementally varying the intensity of the light display in a time ordered sequence, displaying a numerical quantification of the intensity of the light display, and having the subject selectively stop and reset the sequence of varying light intensities to an initial light intensity whenever he first is able to preceive the light display.

The terms and expressions which have been employed here are used as terms of description and not of limitation, and there is no intention, in the use of such terms and expressions, of excluding equivalents of the features shown and described, or portions thereof, it being recognized that various modifications are possible within the scope of the invention claimed.

What is claimed is:

1. Night vision testing apparatus for determining a time based dark adaptation characteristic of a subject comprising means for presenting a light display to the subject at variable intensities, means for automatically and incrementally varying the intensity of the light display in a fixed, time ordered sequence, means for displaying a numerical quantification of the intensity of the light display at each increment and means operable by the test subject for selectively stopping and resetting the sequence of varying light intensities to an initial light intensity when the subject first perceives the displayed light, to give a plurality of independent measurements of the subject's light sensitivity at different points in time during a single dark adaptation process.

2. Night vision testing apparatus as recited in claim 1 wherein the light intensity incremental varying means increases the light intensity in a stepwise, time ordered sequence.

3. Night vision testing apparatus as recited in claim 2 wherein the light intensity incremental varying means doubles the light intensity at each sequential step.

4. Night vision testing apparatus as recited in claim 1 wherein the light display means comprises an extraneous light excluding face mask to be worn by the test subject and a light emitting device mounted in the face mask.

5. Night vision testing apparatus as recited in claim 4 wherein the face mask includes a face plate which is at least partially transparent for a spectral range of light which does not affect the dark adaptation process of the human subject.

6. Night vision testing apparatus as recited in claim 1 wherein the light display means presents a light display at intensities at least below and within the mesopic range of the subject.

7. Night vision testing apparatus as recited in claim 1 wherein the light display includes an electric current operated, light emitting device and the means for incrementally varying the light intensity includes clock pulse generating means, an up/down counter for counting the clock pulses and for producing a plurality of separate output signals representative of the count in the counter, means responsive to the counter output signals for supplying different magnitudes of electrical current to the light emitting device, to thereby produce incremental levels of light intensity in response to the separate counter output signals, and the stopping and resetting means includes means for selectively resetting and recycling the counter.

8. Night vision testing apparatus as recited in claim 1 where, in the absence of being stopped and reset by the test subject, the light intensity varying means sequentially displays each level of light intensity for a first period of time until a preset highest light level is reached, after which the light intensity varying means pauses for a second period of time and then automatically begins the light intensity varying cycle again.

9. A method of testing the time based night vision characteristics of a subject during a single course of dark adaptation comprising the steps of presenting a light display to the subject, automatically, incrementally varying the intensity of the light display in a fixed, time ordered sequence, displaying a numerical quantification of the intensity of the light display at each incremental step and having the test subject selectively stop, reset and recycle the sequence of varying light intensities from an initial light intensity when he first perceives the light display.

10. A method of testing the night vision of a subject as recited in claim 9 wherein the step of incrementally varying the light intensity includes the step of increasing the light intensity in a stepwise, time ordered sequence beginning from a level below the subject's perception.

* * * * *